United States Patent [19]

Ema

[11] Patent Number: 5,140,518

[45] Date of Patent: Aug. 18, 1992

[54] METHOD AND APPARATUS FOR PROCESSING DATA IN MEDICAL INFORMATION COMMUNICATION SYSTEM

[75] Inventor: Takehiro Ema, Ootawara, Japan

[73] Assignee: Kabushiki Kaisha Toshiba, Kawasaki, Japan

[21] Appl. No.: 734,092

[22] Filed: Jul. 23, 1991

Related U.S. Application Data

[63] Continuation of Ser. No. 426,806, Oct. 26, 1989, abandoned.

[30] Foreign Application Priority Data

Oct. 28, 1988 [JP] Japan .................. 63-272439

[51] Int. Cl.$^5$ .............................................. G06F 15/00
[52] U.S. Cl. ........................... 364/413.01; 364/413.13
[58] Field of Search .............. 364/419, 413.01, 413.02, 364/413.13; 395/140, 144, 145, 146, 147, 148, 149; 382/2, 4, 6

[56] References Cited

U.S. PATENT DOCUMENTS

| | | | |
|---|---|---|---|
| 3,872,448 | 3/1975 | Mitchell, Jr. .................. | 364/413.01 |
| 4,604,653 | 8/1986 | Shimizu . | |
| 4,672,683 | 6/1987 | Matsueda . | |
| 4,713,789 | 12/1987 | Suzuki ................................. | 382/49 |
| 4,737,912 | 4/1988 | Ichikawa ........................ | 364/413.01 |
| 4,760,390 | 7/1988 | Maine et al. ....................... | 340/747 |
| 4,817,050 | 3/1989 | Komatsu et al. .................... | 364/518 |
| 4,833,625 | 5/1989 | Fisher et al. .................... | 364/413.13 |
| 4,893,270 | 1/1990 | Beck et al. ........................ | 364/400 |
| 4,945,477 | 7/1990 | Edwards ........................ | 364/413.06 |
| 4,958,283 | 9/1990 | Tawara et al. .................. | 364/413.13 |

FOREIGN PATENT DOCUMENTS

GB 2164771A 3/1986 United Kingdom .

OTHER PUBLICATIONS

Cox et al., Computer Networks for Image Management in Radiology: An Overview, CRC Critical Review in Diagnostic Imaging, vol. 25, No. 4, 1986, pp. 333–371.
Lemke et al., Work Stations for Computer-Graphic Display in Medical Imaging, Biomedizinische Technik, pp. 143–149.

*Primary Examiner*—Dale M. Shaw
*Assistant Examiner*—Laura Brutman
*Attorney, Agent, or Firm*—Finnegan, Henderson, Farabow, Garrett and Dunner

[57] ABSTRACT

In a medical information communication system, image data and image addition data acquired by modalities are stored in a database. An unread examination list and a read examination list are produced in the database, and are transferred to work stations during a reading operation. List data for the read examination list is arranged in accordance with a desired priority order. Image data or the like associated with each examination list is transferred to magnetic disks from an optical disk.

11 Claims, 13 Drawing Sheets

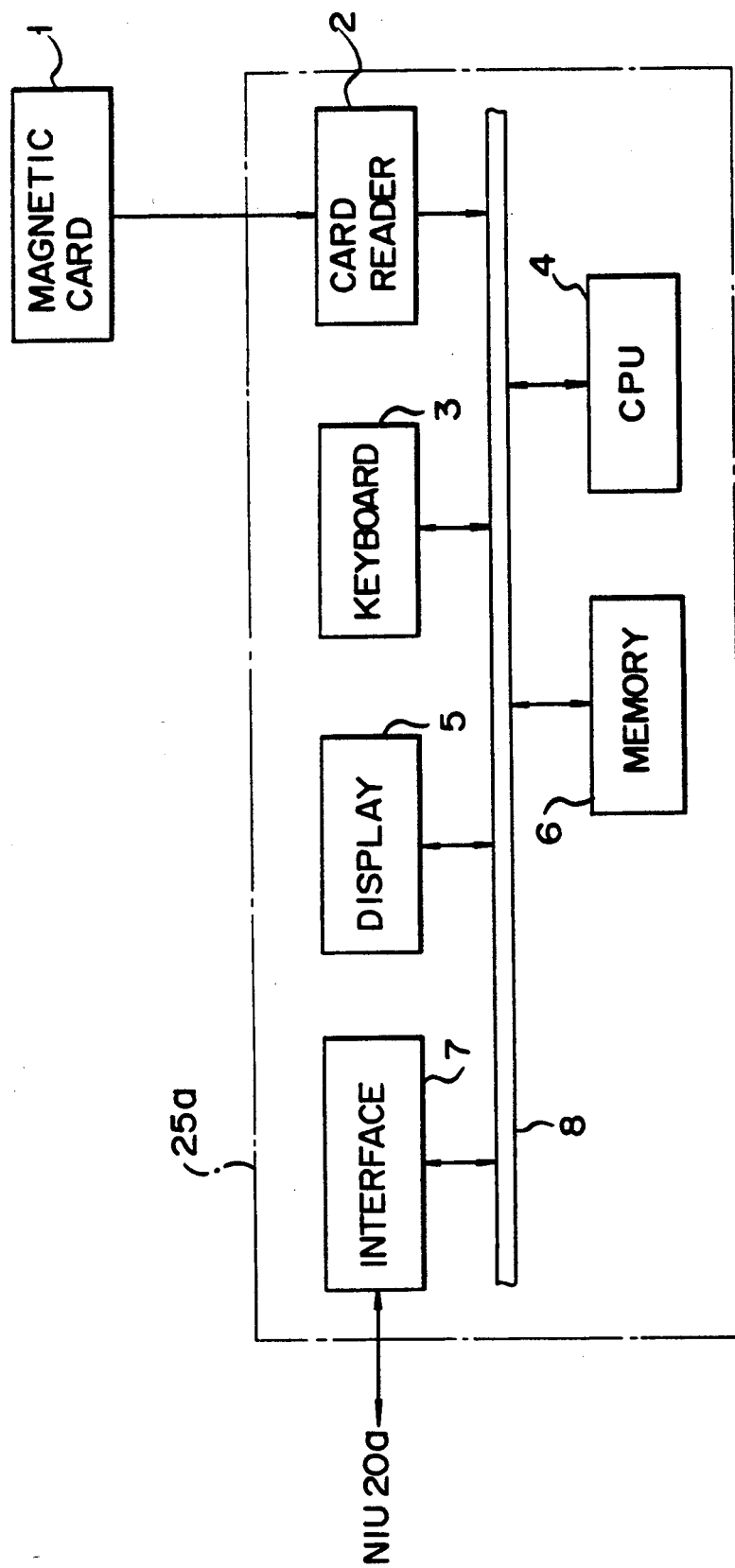
F I G. 2

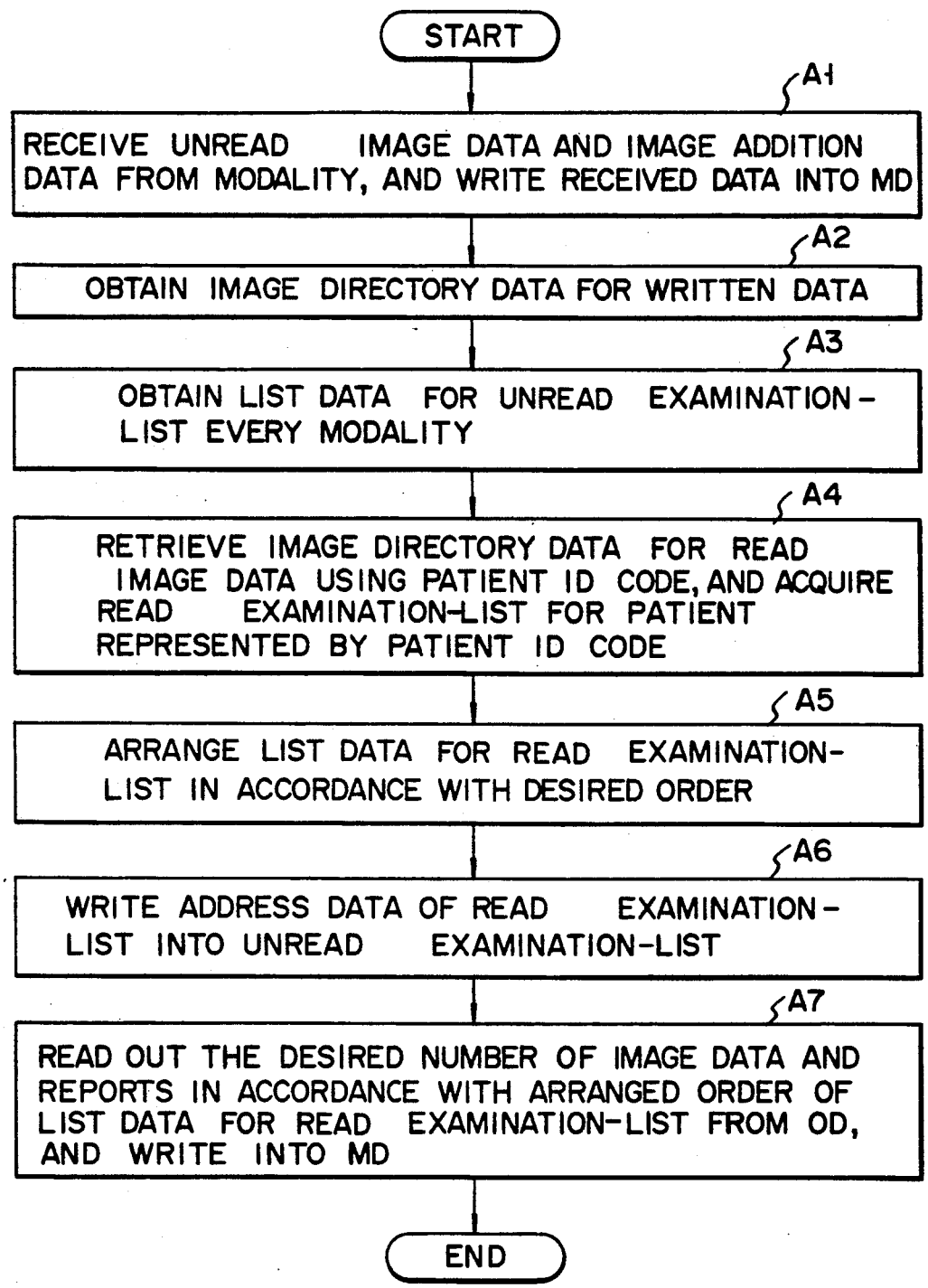
F I G. 4

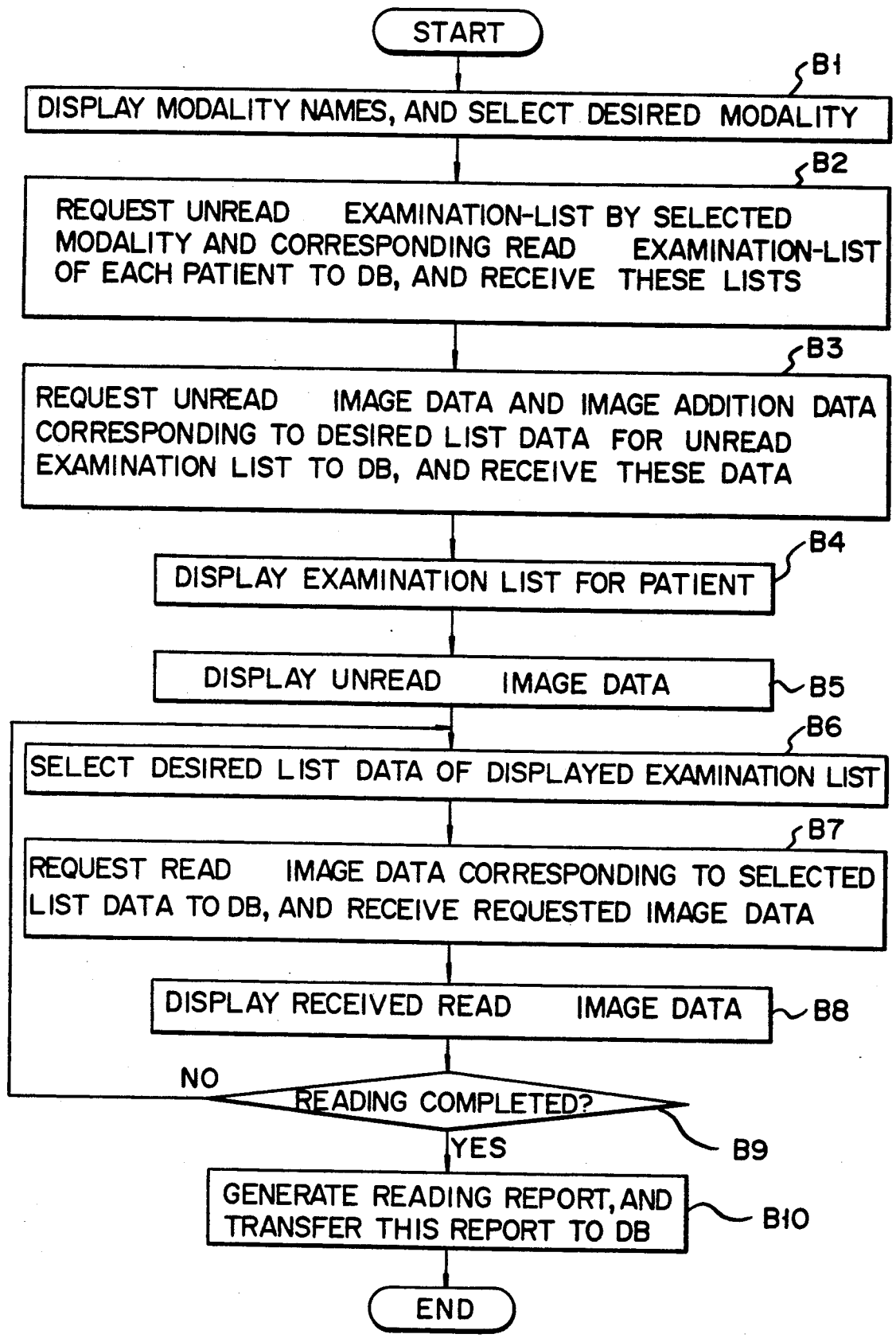
F I G. 5

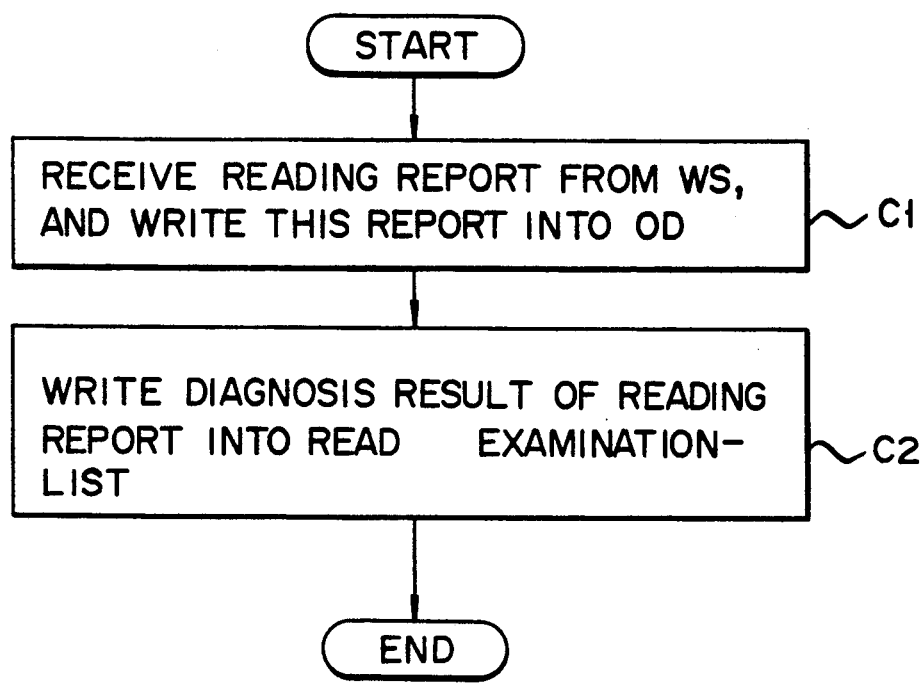
F I G. 6

| EXAMINATION INFORMATION | MODALITY ID CODE | M1, M2 ----- |
|---|---|---|
| | PORTION ID CODE | S1, S2 ----- |
| | EXAMINATION DATE | K880910, K880911,---- |
| PATIENT INFORMATION | PATIENT ID CODE | P1, P2 ----- |
| | SEX | M (MALE) F (FEMALE) |
| | DATE OF BIRTH | B520118, B550418,---- |
| IMAGE INFORMATION | IMAGE MEMORY AREA | 200, 300, ---- |
| | IMAGE MATRIX CODE | MT128, MT256, --- |

F I G. 7

| EXAMINATION ID CODE | IMAGE ADDITION DATA | MEMORY ADDRESS | MEMORY AREA |
|---|---|---|---|
| I1 | --- | --- | --- |
| I2 | --- | --- | --- |
| I3 | --- | --- | --- |
| ------- | ------ | ------ | ------ |

FIG. 8

| EXAMINATION ID CODE | MODALITY ID CODE | PORTION ID CODE | PATIENT ID CODE | DOCTOR ID CODE | EXAMINATION DATE | UNREAD EXAMINATION-LIST ADDRESS |
|---|---|---|---|---|---|---|
| I25 | M2 | S2 | P100 | 124 | K880927 | --- |
| I28 | M2 | S3 | P105 | 124 | K881010 | --- |
| --- | --- | --- | --- | --- | --- | --- |

| UNREAD EXAMINATION-LIST BY CT | UNREAD EXAMINATION-LIST BY MR |
| UNREAD EXAMINATION-LIST OF HEAD | UNREAD EXAMINATION-LIST OF CHEST |
| UNREAD EXAMINATION-LIST FOR DOCTOR A | UNREAD EXAMINATION-LIST FOR DOCTOR B |

| EXAMINATION ID CODE | MODALITY ID CODE | PORTION ID CODE | PATIENT ID CODE | EXAMINATION DATE | |
|---|---|---|---|---|---|
| I5 | M1 | S5 | P100 | K860712 | --- |
| I8 | M1 | S4 | P100 | K870303 | --- |
| -------- | -------- | -------- | -------- | -------- | -------- |

FIG. 11

| DOCTOR ID CODE | IMAGE ADDITION DATA | | |
| --- | --- | --- | --- |
| | PATIENT ID CODE | PORTION ID CODE | MODALITY ID CODE |
| 123 | P1 | S2 | — |
| 124 | P1 | — | M1 |
| 125 | P2 | S3 | — |
| 126 | P2 | S3 | M2 |
| ----- | ----- | ----- | ----- |

F I G. 12

PATIENT NAME : ICHIRO TOSHIBA    SEX : MALE    AGE : 60

EXAMINATION (SYMBOL ✕ REPRESENTS UNREAD STATE)
LIST

| | EXAMINATION PORTION | MODALITY | EXAMINATION DATA | DOCTOR NAME | DIAGNOSIS RESULT |
|---|---|---|---|---|---|
| ✕ 1. | HEAD | MR | 10/5/88 | TANAKA | |
| 2. | HEAD | MR | 9/25/88 | TANAKA | BRAIN TUMOR |
| 3. | HEAD | CT | 9/30/88 | SATO | BRAIN TUMOR |
| 4. | HEAD | CT | 9/20/88 | SATO | BRAIN TUMOR |
| 5. | HEAD | CT | 5/17/88 | SATO | BRAIN TUMOR |
| 6. | CHEST | X-RAY | 9/15/87 | SUZUKI | NORMAL |
| 7. | ABDOMEN | X-RAY | 6/10/86 | ITO | NORMAL |
| ---- | ---- | ---- | ---- | ---- | ---- |

F I G. 13

METHOD AND APPARATUS FOR PROCESSING DATA IN MEDICAL INFORMATION COMMUNICATION SYSTEM

This application is a continuation of application Ser. No. 07/426,806, filed Oct. 26, 1989 now abandoned.

BACKGROUND OF THE INVENTION

1. Field of the Invention

The present invention relates to a method and apparatus for processing data in a medical information communication system.

2. Description of the Related Art

A PACS (Picture Archiving and Communication System) is constructed by modalities, network interface units, a star coupler, work stations, a database, or the like.

Each modality includes by a medical diagnosis apparatus, such as an X-ray diagnosis apparatus, MRI (Magnetic Resonance Imaging) apparatus, or ultrasonic diagnosis apparatus. Image data of a patient acquired by each modality is stored in a database. This image data is transferred via a star network constructed of a star coupler, or the like. Each work station comprises a display and a console. The reading operation for image data specified through the console is requested by a doctor, a radiologist, or the like. The reading operation represents a diagnosis operation for the image data of a patient.

During the reading operation, retrieval data is input via the console and an examination list yet to be read (hereinafter referred to as an unread examination list) is displayed on the display. The unread examination list includes image addition data concerning image data yet to be read (hereinafter referred to as unread image data). The image addition data for a plurality of patients is written on this examination list. By referring to the examination list, a doctor may input an image number for specifying image data and perform a diagnosis by displaying image data corresponding to the input image number on the display.

In referring to previous image data (hereinafter referred to as read image data), a previous patient examination list (hereinafter referred to as a read examination list) for a desired patient is displayed on the display by inputting a patient ID code and retrieval data. The read examination list includes image addition data concerning the read image data. By inputting an image number, corresponding image data is displayed on the display. Accordingly, referring to the read image data, reading operation for unread image data is performed. Read image data of a patient is often used during the reading operation.

For a database, an optical disk is used as a long-term storage medium for image data. On the other hand, a magnetic disk or an IC (Integrated Circuit) memory is used as a short-term or temporary storage medium. With a work station, it is desirable to promptly display an image upon request, so that a magnetic disk and/or an IC memory is used as a storage medium.

Such a magnetic disk and IC memory have performance limits and it is not possible to determine in advance how many read image data of a patient are to be stored. Therefore, it is necessary to set a priority order for displaying image data. In other words, it is necessary to transfer in advance image data to be immediately displayed from a database to a work station by the priority order.

In displaying a read examination list, it is desirable to arrange the images in order according to an image ID code corresponding to image data having a high probability for selection. This is because it is usually impossible to display the entire examination list for a desired patient on a limited display screen.

Further, when continuously reading unread image data of a plurality of patients, an unread examination list is produced in a database in advance, and unread image data and the like are automatically prepared for transfer, thus reducing or eliminating the operation of image selection by a doctor.

In view of the above, there is a demand for an apparatus which can improve the efficiency of the doctor.

SUMMARY OF THE INVENTION

It is an object of the present invention to provide a method and apparatus for processing data in a medical information communication system.

According to one aspect of the present invention, there is provided a method for processing data in a medical information communicating system, the method comprising the steps of:

storing image data and image addition data, the image data including first and second image data, the image addition data including a plurality of parameters each corresponding to the first and second image data;

generating a first examination list in accordance with the parameters corresponding to the first image data, and a second examination list in accordance with a desired parameter and the parameters corresponding to the second image data, the second examination list having a plurality of list data;

arranging the list data for the second examination list in accordance with a desired order, thereby obtaining third examination list having the arranged list data; and displaying the first and third examination lists, the first and second image data.

According to another aspect of the present invention, there is provided an apparatus for processing data in a medical information communicating system, the apparatus comprising:

storing means for storing image data and image addition data, the image data including first and second image data, the image addition data including a plurality of parameters each corresponding to the first and second image data;

generating means for generating a first examination list in accordance with the parameters corresponding to the first image data, and a second examination list in accordance with a desired parameter and the parameters corresponding to the second image data, the second examination list having a plurality of list data;

arranging means for arranging the list data for the second examination list in accordance with a desired order, thereby obtaining third examination list having the arranged list data; and displaying means for displaying the first and third examination lists, the first and second image data.

BRIEF DESCRIPTION OF THE DRAWINGS

FIG. 2 is a block diagram illustrating a work station in a PACS;

FIG. 4 is a flowchart of a reading operation preparing process in a database;

FIG. 5 is a flowchart of a reading operation process in a work station;

FIG. 6 is a flowchart of a reading operation result storing process in a database;

FIG. 7 is a diagram illustrating the contents of image addition data;

FIG. 8 is a diagram illustrating the contents of image directory data;

FIG. 9 is a diagram illustrating the contents of an unread examination list;

FIGS. 10A to 10C are diagrams illustrating the classification of unread examination lists;

FIG. 11 is a diagram illustrating the contents of a read examination list;

FIG. 12 is a diagram illustrating image addition data for every doctor ID code; and FIG. 13 is a display example illustrating an examination list of a patient in a work station.

DETAILED DESCRIPTION OF THE PREFERRED EMBODIMENTS

Figure 1:
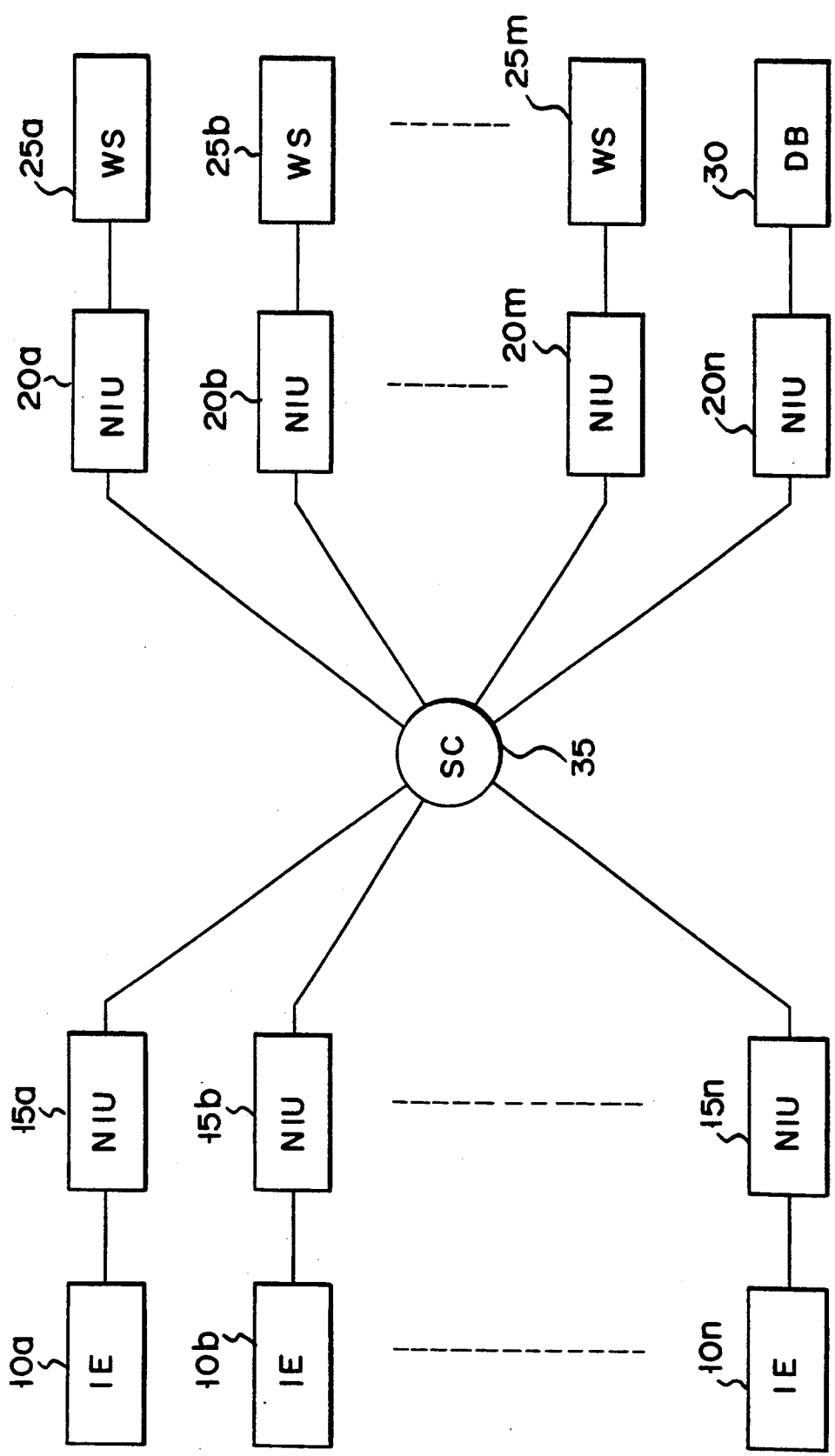
FIG. 1 is a block diagram illustrating the arrangement of a PACS.

A preferred embodiment of the present invention will now be described referring to the accompanying drawings. As shown in FIG. 1, a PACS according to this embodiment comprises modalities (IEs) 10a, 10b, ..., 10n, network interface units (NIUs) 15a, 15b, ..., 15n, 20a, 20b, ..., 20m, 20n, a star coupler (SC) 35, work stations (WSs) 25a, 25b, ..., 25m, and a database (DB) 30.

The IEs 10a to 10n include medical diagnosis apparatus (modality) such as an X-ray diagnosis apparatus, an MRI apparatus, or an ultrasonic diagnosis apparatus. Image data acquired by each apparatus is stored in the DB 30. Image data is transferred via a star network constructed by the SC 35, etc. The WSs 25a to 25m each comprise a display and a console, and reading operation may be performed at each work station. The reading operation allows diagnosis operation of the image data of a patient.

As shown in FIG. 2, the WS 25a comprises a card reader 2 for reading data stored in a magnetic card (MC 1 serving as a portable recording medium, a keyboard 3, a memory 6, a CPU (Central Processing Unit) 4, a display 5, an interface 7, and a bus 8.

Figure 3:
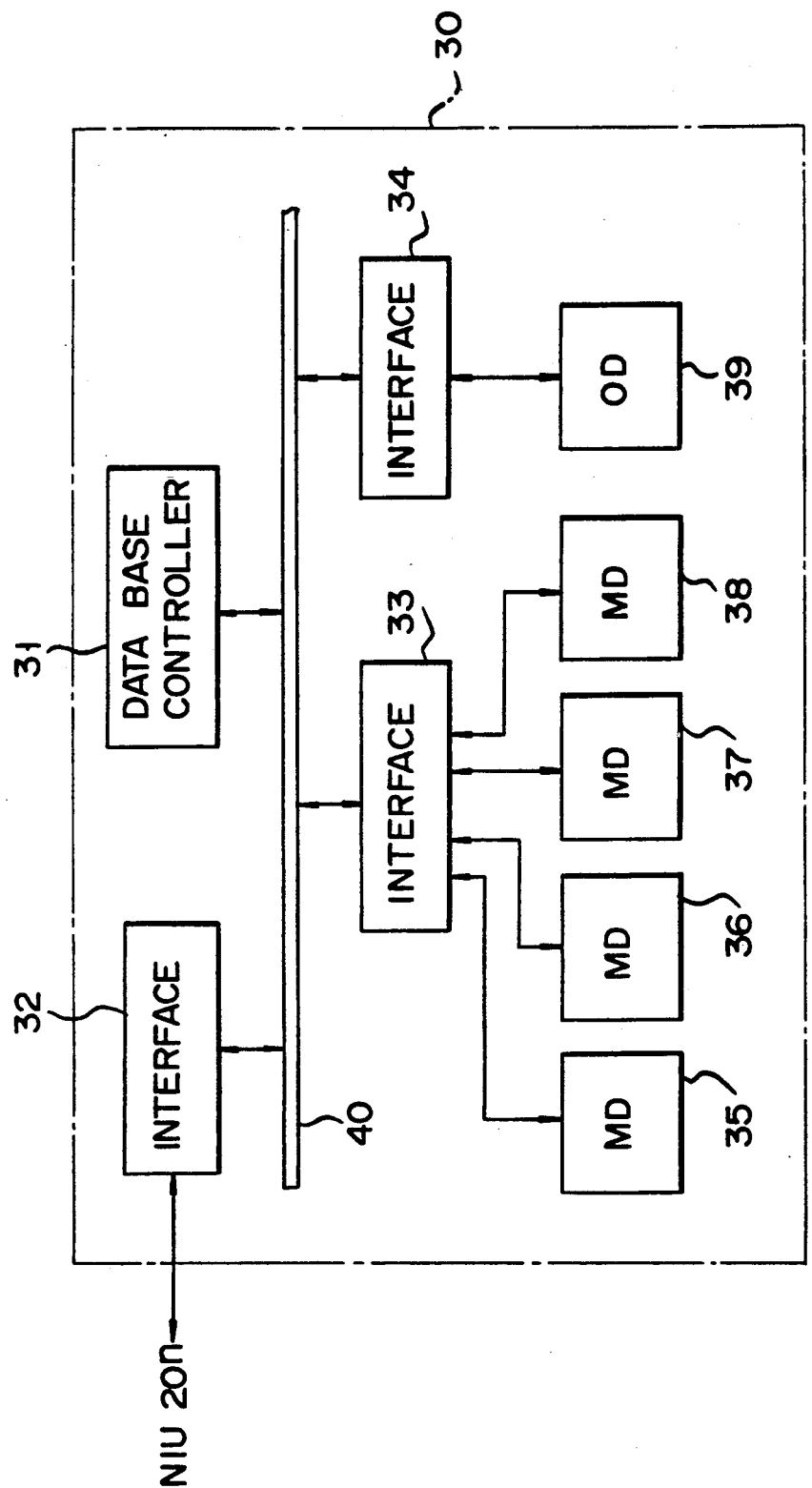
FIG. 3 is a block diagram illustrating a database in a PACS.

As shown in FIG. 3, the DB 30 is constructed by an optical disk (OD) 39 serving as a main storage device, magnetic disks (MDs) 35 to 38 serving as auxiliary storage device, a database controller 31, interfaces 32 to 34, and a bus 40. In accordance with a request form a work station, the database controller 31 controls data transfer between the work station and the OD 39 or the MDs 35 to 38, and the operation of the OD 39 and MDs 35 to 38.

The MD 35 stores directory data and image addition data, the MD 36 an examination list, the MD 37 a reading report, and the MD 38 image data.

The operation of present system will be described below.

In the following description, the flowcharts shown in FIGS. 4 to 6 will be referred to for explaining a reading operation preparing process in a database, a reading operation process in a work station, and a reading operation result storing process in the database.

In the reading operation preparing process in the database, as shown in FIG. 4, image data and image addition data transferred from a modality are received and written in MDs in step A1. The contents of the image addition data is illustrated in FIG. 7. The image addition data includes information such as an image ID code and a doctor ID code in addition to those shown in FIG. 7.

In step A2, image directory data for data written in the MD is obtained; this image directory data is additionally stored in a directory data storing MD. As shown in FIG. 8, the image directory data includes an examination ID code, image addition data, data representing a memory address, and data representing a memory area.

In step A3, list data for an examination list yet to be read (hereinafter referred to as an unread examination list) is obtained for each modality (see FIG. 9). This list data includes some information of the image addition data. The unread examination list includes image addition data concerning image data yet to be read (hereinafter referred to as unread image data).

It is desirable that the number and classification of unread examination lists are set in accordance with the circumstances of each hospital. For instance, there may be an unread examination list for each modality (FIG. 10A), an unread examination list for each examination portion (FIG. 10B) and an unread examination list for each doctor (FIG. 10C). The present embodiment will be described with reference to the case where an unread examination list for each modality is prepared.

In step A4, image directory data of previous image data (hereinafter referred to as read image data) is retrieved using a patient ID code as retrieval data, and a previous patient examination list (hereinafter referred to as a read examination list) of the patient specified by the patient ID code is acquired (see FIG. 11). The read examination list includes image addition data concerning the read image data.

In step A5, list data for the read examination list is arranged in accordance with a desired priority order.

Data concerning the priority order is set in advance in the DB. This priority order is set so as to arrange the list data in an order based on the probability that with image data having a high probability that it will be referred to by a doctor, a radiologist, and the like. For instance, the priority order may be set as follows:

(1) Same patient, same examination portion, and same modality.

(2) Same patient, same examination portion, and other modality.

For the same priority order, the list data are arranged from a new examination date.

This priority order may differ depending on doctors and the like. As shown in FIG. 12, the priority order can be set by storing in advance data concerning the priority order in a magnetic card or the like carried by a doctor, and reading out the data from the magnetic card as needed.

In step A6, address data of the read examination list is written on an unread examination list (see FIG. 9).

In step A7, image data and reports for a desired number of examinations are read out from an OD in accordance with the arranged order of the list data for the read examination list and are written in the MD.

Reading operation preparation in a database will be completed through the above sequence.

In the reading operation in a work station as shown in FIG. 5, modality names are displayed and the desired modality associated with a doctor in charge is selected in step B1.

In step B2, an unread examination list by the selected modality and a corresponding examination list of each patient are requested to the DB and these lists are received from the DB.

In step B3, unread image data and image addition data corresponding to desired list data, for example, head list data, for the unread examination list are requested from the DB, and this data is received from the DB.

In step B4, an examination list for a desired patient is displayed as shown in FIG. 13.

In step B5, unread image data is displayed.

In step B6, the desired list data is selected from the displayed examination list.

In step B7, image data corresponding to the selected list data is requested from the DB and the requested image data is then received.

In step B8, the received read image data is displayed

In step B9, it is determined whether or not the reading operation has been completed. If the reading operation has not been completed yet, the sequence following step B6 will be repeated. On the other hand, if the reading operation has been completed, a reading report is produced and transferred to the DB (step B10).

The reading operation process in the work station will be completed with the above sequence.

In the result storing process of the reading operation in the database as shown in FIG. 6, the reading report transferred from the WS is received and stored in the OD in step C1.

In step C2, the diagnosis results of the reading report are written on the examination list.

The process shown in FIG. 6 will be completed through the above two steps.

By executing the processes shown in FIGS. 4 to 6, a reading operation for a desired patient is completed.

According to this embodiment, as described above, an unread examination list and a read examination list are produced by specific image addition data (patient ID code), so that the examination efficiency can be improved.

In a database, during production of the unread examination list and read examination list, image data and a report for each examination list, are transferred from an OD to an MD. The image data and report which are likely to be referenced, are not only transferred to the MD from the OD but are also transferred to the memory of the work station from the MD. Therefore, when the image data and report are requested, they can be displayed quickly, thus improving the reading operation efficiency.

Further, selection of a referred read image is facilitated by arranging list data of a read examination list in accordance with a desired priority order. This priority order can be set in advance in the database or can be set for each doctor. Rearrangement of the list data can be performed in the data base as well as on the work station.

The preferred embodiment of the present invention has been described. The invention is not limited to the disclosed embodiment, can be modified in various manners within the scope of the invention.

What is claimed is:

1. A method for processing data in a medical information communication system, the method comprising the steps of:

storing image data and image addition data, the image data including first and second image data, the image addition data including a plurality of parameters each corresponding to one of the first and second image data;

generating a first examination list in accordance with the parameters corresponding to the first image data, and a second examination list in accordance with a desired parameter and the parameters corresponding to the second image data, the second examination list having a plurality of list data;

arranging the list data of the second examination list in accordance with a desired order, thereby obtaining a third examination list having an arranged set of list data; and displaying the first and third examination list and the first and second image data.

2. The method according to claim 1, wherein the first image data includes image data not yet read for diagnosis.

3. The method according to claim 1, wherein the second image data includes previously read image data for diagnosis.

4. The method according to claim 1, wherein the desired order is determined by using the parameters.

5. An apparatus for processing data in a medical information communication system, the apparatus comprising:

storing means for storing image data and image addition data, the image data including first and second image data, the image addition data including a plurality of parameters each corresponding to one of the first and second image data;

generating means for generating a first examination list in accordance with the parameters corresponding to the first image data, and a second examination list in accordance with a desired parameter and the parameters corresponding to the second image data, the second examination list having a plurality of list data;

arranging means for arranging the list data of the second examination list in accordance with a desired order, thereby obtaining a third examination list having an arranged set of list data; and displaying means for displaying the first and third examination lists and the first and second image data.

6. The apparatus according to claim 5, wherein the storing means includes an optical disk and a magnetic disk.

7. The apparatus according to claim 6, wherein the image data is transferred from the optical disk to the magnetic disk in accordance with the desired order.

8. An apparatus for processing data in a medial information communication system, the apparatus comprising:

acquiring means for acquiring image data of a patient and image addition data, the image data including first image data and second image data, the image addition data including a plurality of parameters each corresponding to one of the first and second image data;

storing means for storing the image data and the image addition data;

generating means for generating first and second examination lists for the patient in accordance with the image data and the image addition data; and displaying means for displaying the stored image data and the generated first and second examination lists;

wherein the generating means includes:

means for generating the first examination list in accordance with the parameters corresponding to the first image data, and generating the second examination list having a plurality of list data in accordance with a desired parameter corresponding to the first image data and the parameters corresponding to the second image data; and means for arranging the list data for the second examination list in accordance with a desired order, thereby obtaining the second examination list having an arranged set of list data.

9. The apparatus according to claim 8, wherein the storing means includes an optical disk and a magnetic disk.

10. The apparatus according to claim 9, wherein the image data is transferred from the optical disk to the magnetic disk in accordance with the desired order.

11. An information communication system, comprising:

database means for storing a plurality of sets of image data and a plurality of sets of image addition data, each image data set including read image data and unread image data, for generating an unread examination list in accordance with the image addition data set for the unread image data, for generating a read examination list having a plurality of list data in accordance with the image addition data set for the unread image data and for the read image data, and for arranging the list data in accordance with a desired order to obtain the read examination list having an arranged set of list data; and work station means for accessing the database means to display the unread examination list and the unread image data, and wherein the read examination list and the read image data are retrieved by the workstation means from the database means when the unread examination list and the unread image data are displayed.

* * * * *